US00PP09521P

United States Patent [19]

Trees

[11] Patent Number: Plant 9,521

[45] Date of Patent: Apr. 23, 1996

[54] NEW GUINEA IMPATIENS NAMED 'BFP-523 DEEP RED'

[75] Inventor: Scott C. Trees, Arroyo Grande, Calif.

[73] Assignee: Geo. J. Ball, Inc., West Chicago, Ill.

[21] Appl. No.: 422,231

[22] Filed: Apr. 14, 1995

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named 'BFP-523 Deep Red' is provided. This new cultivar was the result of a controlled breeding program wherein the 'BFP-364 Deep Coral' cultivar (U.S. Plant patent application Ser. No. 338,162, filed Nov. 8, 1994) was pollinated by a plant designated BFP-307 (non-patented in the United States). The new cultivar forms large round deep red flowers displaying an iridescent appearance, forms shiny dark green foliage, exhibits a good basal branching character, and exhibits a medium upright mounded growth habit. The new cultivar can be readily distinguished from the 'BFP-347 Red' cultivar (U.S. Plant patent application Ser. No. 337, 529, filed Nov. 8, 1994).

1 Drawing Sheet

SUMMARY OF THE INVENTION

The present invention provides a new and distinctive Impatiens plant, botanically known as New Guinea Impatiens, and hereinafter referred to by the cultivar name 'BFP-523 Deep Red'.

The new cultivar is the product of a planned breeding program. More specifically, the breeding program which resulted in the production of the new cultivar was carried out in a controlled environment during 1992 at Arroyo Grande, Calif., U.S.A. The female parent (i.e., the seed parent) was the 'BFP-364 Deep Coral' (U.S. Plant patent application Ser. No. 338,162, filed Nov. 8, 1994) which exhibits large dark coral flowers with variegated bronze foliage. The male parent (i.e., the pollen parent) was a plant designated BFP-307 (non-patented in the United States) which exhibits large bright red flowers with medium green foliage. The parentage of the new cultivar can be summarized as follows:

'BFP-364 Deep Coral'×BFP-307.

The seeds resulting from the above pollination were sown and plantlets were obtained which were physically and biologically different from each other. Selective study resulted in the identification of a single plant of the new cultivar. This plant had large round deep red flowers with shiny dark green foliage and initially was designated BFP-523. Another progency of the same cross named 'BFP-467 Cherry Red' forms the subject matter of U.S. Plant patent application Ser. No. 08/422,228, filed concurrently herewith.

It was found that the new cultivar of the present invention:

(a) exhibits attractive large deep red flowers, (b) forms shiny dark green foliage, (c) exhibits a good basal branching character, and (d) exhibits a medium upright mounded growth habit.

Asexual reproduction of the new cultivar by terminal or stem cuttings taken during 1992, at Arroyo Grande, Calif., U.S.A., has demonstrated that the characteristics of the new cultivar as herein described are firmly fixed and are retained through successive generations of such asexual propagation.

The 'BFP-523 Deep Red' cultivar has not been observed under all possible environmental conditions to date. Accordingly, it is possible that the phenotype may vary somewhat with variations in the environment, such as temperature, light intensity, and day length.

When the new cultivar of the present invention is compared to the 'BFP-347 Red' (U.S. Plant patent application Ser. No. 337,529, filed Nov. 8, 1994), it is found that the new variety exhibits large flowers (e.g., approximately 5.5 to 6.1 cm. in length×approximately 5.5 to 6.1 cm. in width vs. approximately 5.2 to 5.7 cm. in length×approximately 4.9 to 5.6 cm. in width, and smaller leaves (e.g., approximately 8.7 to 10.5 cm. in length×approximately 3.0 to 3.5 cm. in width vs. approximately 10.0 to 11.0 cm. in length×approximately 3.9 to 4.3 cm. in width).

When plant material of the 'BFP-523 Deep Red' cultivar is subjected to standard random amplified polymorphic DNA marker analysis (RAPD) using polymerase chain reaction (PCR) and a known unique set of DNA primers, it is found to exhibit a different fingerprint map when compared to that of 'BFP-347 Red' cultivar which confirms its genetic distinctiveness.

Plants of the new cultivar will be marketed under the Celebration trademark by Geo. J. Ball, Inc.

BRIEF DESCRIPTION OF THE PHOTOGRAPH

The accompanying photograph of FIG. 1 shows as nearly true as it is reasonably possible to make the same in a color illustration of this character, a typical specimen of an overall plant of the new cultivar. The typical flower and foliage characteristics are exhibited. The plant was grown to a greenhouse at West Chicago, Ill., U.S.A.

DETAILED DESCRIPTION

Figure 1:
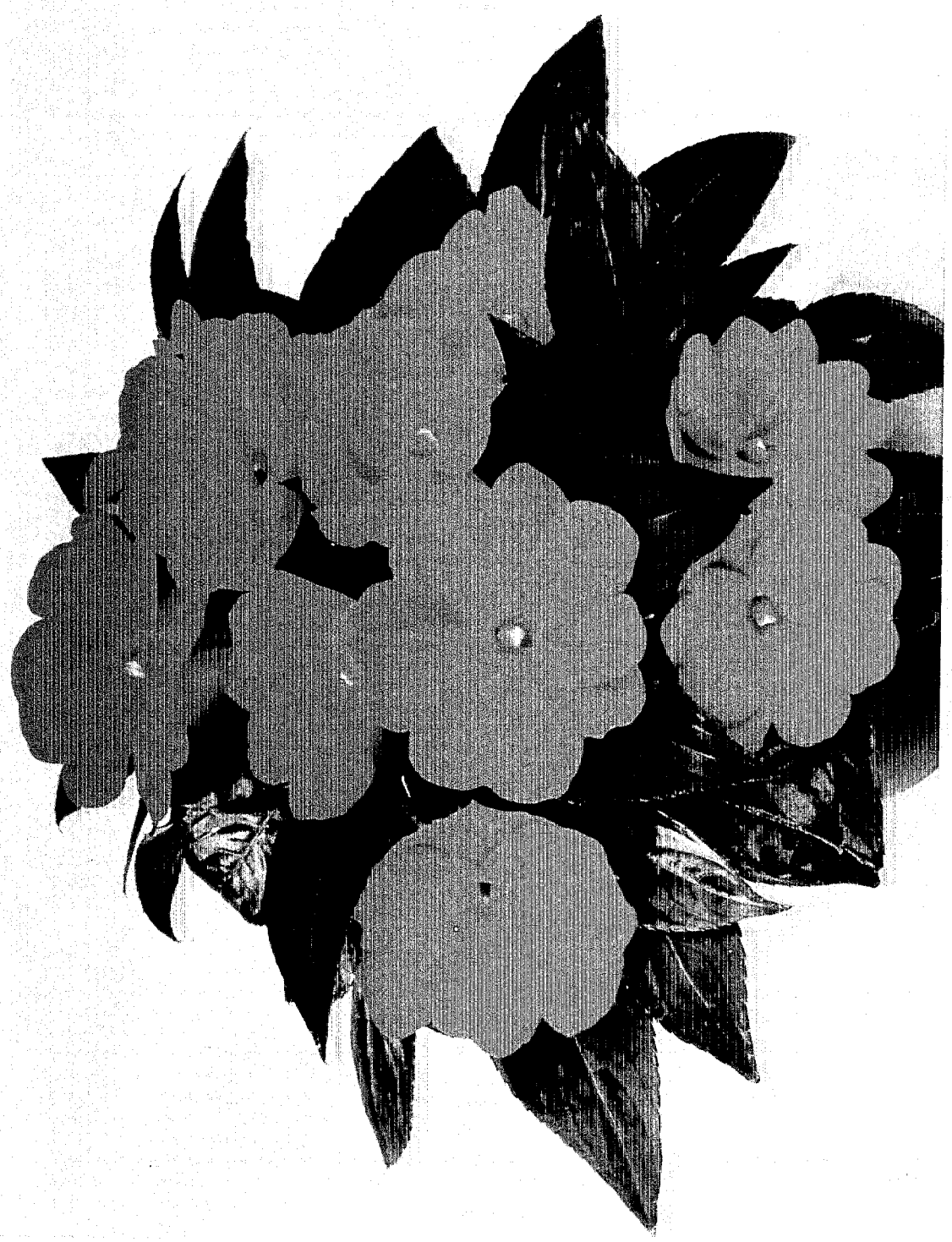

The chart used in the identification of colors described herein is the R.H.S. Colour Chart of The Royal Horticultural Society, London, England. The color values were determined on Jan. 3, 1995. The readings were taken between 1:00 and 1:45 p.m. under 2,000 footcandles of light at West Chicago, Ill., U.S.A. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant Description:

*Habit of growth.*—Basal branching.

*Form.*—Medium upright mounded. A mature plant commonly measured approximately 7 to 10 cm. in height and approximately 20 to 24 cm. in width compared to approximately 9.5 to 12 cm. in height and approximately 19 to 24 cm. in width for the 'BFP-347 Red' cultivar.

*Foliage.*—The configuration is narrow and lanceolate. The leaves of the new cultivar commonly measure approximately 8.7 to 10.5 cm in length and approximately 3.0 to 3.5 cm. in width while those of the 'BFP-347 Red' cultivar commonly measure approximately 10 to 11 cm. in length and approximately 3.9 to 4.3 cm. in width. The foliage of the new cultivar is slightly darker than Green Group 136A (adaxial) and Green Group 137C (abaxial). This can be compared to Green Group 139A (adaxial) and Green Group 138A (abaxial) for the 'BFP-347 Red' cultivar. The stem color is Yellow-Green Group 145C for both the 'BFP-523 Deep Red' and the 'BFP-347 Red' cultivars.

Flower description:

*Flowering habit.*—Freely flowering.

*Natural flowering season.*—Throughout the year in a greenhouse environment.

*Flowers borne.*—Above the foliage arising from leaf axils.

*Flower color.*—Red Group 45A (adaxial) and Red Group 45D (abaxial). This can be compared to Red Group 45A (adaxial) and Red Group 45C (abaxial) for the 'BFP-347 Red' cultivar.

*Quantity of flowers.*—Approximately 8 to 10 per stem compared to 7 to 9 per branch for the 'BFP-347 Red' cultivar.

*Number of petals.*—Five.

*Flower size.*—Approximately 5.5 to 6.1 cm. in length and approximately 5.5 to 6.1 cm. in width. This can be compared to a length of approximately 5.2 to 5.7 cm. and a width of approximately 4.9 to 5.6 cm. for the 'BFP-347 Red' cultivar.

*Nectary length.*—Approximately 5.3 to 5.5 cm. which can be compared to approximately 5.0 to 5.5 cm. for the 'BFP-347 Red' cultivar.

*Nectary color.*—Red Group 53A for both the 'BFP-523 Deep Red' and the 'BFP-347 Red' cultivars.

*Reproductive organs.*—The anthers are fused together forming one organ that surrounds the pistil. Generally the anthers shed pollen prior to the stigma becoming receptive. The pollen color is Yellow-Orange Group 19D for the new cultivar. The stigma color is Yellow-Green Group 154D. The ovary color is Yellow-Green Group 144C.

I claim:

1. A new and distinct cultivar of New Guinea Impatiens plant named 'BFP-523 Deep Red' substantially as herein shown and described, which:

(a) exhibits attractive large deep red flowers, (b) forms shiny dark green foliage, (c) exhibits a good basal branching character, and (d) exhibits a medium upright mounded growth habit.

* * * * *